US009072718B2

(12) United States Patent
Okubo et al.

(10) Patent No.: US 9,072,718 B2
(45) Date of Patent: Jul. 7, 2015

(54) BURDOCK FRUIT EXTRACT CONTAINING ARCTIGENIN AND METHOD FOR PRODUCING SAME

(71) Applicants: Kracie Pharma, Ltd., Tokyo (JP); National Cancer Center, Tokyo (JP); National University Corporation University of Toyama, Toyama (JP)

(72) Inventors: Toshiki Okubo, Toyama (JP); Satoshi Yomoda, Toyama (JP); Takafumi Fuse, Toyama (JP); Takanori Kawashima, Toyama (JP); Hiroyasu Esumi, Chiba (JP); Chika Miyoshi, Chiba (JP); Shigetoshi Kadota, Toyama (JP)

(73) Assignees: National University Corporation University of Toyama, Toyama (JP); Kracie Pharma, Ltd., Tokyo (JP); National Cancer Center, Tokyo (JP)

( * ) Notice: Subject to any disclaimer, the term of this patent is extended or adjusted under 35 U.S.C. 154(b) by 42 days.

(21) Appl. No.: 13/849,302

(22) Filed: Mar. 22, 2013

(65) Prior Publication Data

US 2014/0037770 A1 Feb. 6, 2014

Related U.S. Application Data

(63) Continuation-in-part of application No. PCT/JP2011/072049, filed on Sep. 27, 2011.

(30) Foreign Application Priority Data

Sep. 27, 2010 (JP) ................................ 2010-215118

(51) Int. Cl.

| | |
|---|---|
| ***A01N 65/00*** | (2009.01) |
| ***A61K 36/28*** | (2006.01) |
| ***A61K 31/365*** | (2006.01) |
| ***A61K 31/7048*** | (2006.01) |
| ***C07D 307/33*** | (2006.01) |

(52) U.S. Cl.

CPC ............... *A61K 36/28* (2013.01); *A61K 31/365* (2013.01); *A61K 31/7048* (2013.01); *C07D 307/33* (2013.01); *A61K 2236/19* (2013.01)

(58) Field of Classification Search

CPC ......................... A61K 36/00; A61K 2236/333
USPC ........................................................ 424/725
See application file for complete search history.

(56) References Cited

FOREIGN PATENT DOCUMENTS

| | | | | |
|---|---|---|---|---|
| CN | 1500265 A | 2/2004 | .............. | C12P 17/04 |
| CN | 1560265 A | 2/2004 | .............. | C12P 17/04 |
| CN | 1491674 * | 4/2004 | | |
| CN | 101392279 A | 3/2009 | .............. | C12P 17/04 |
| EP | 2 412377 A1 | 2/2010 | .............. | A61K 9/14 |
| KR | 1020080107794 | 12/2008 | ............ | A61K 36/28 |

OTHER PUBLICATIONS

Awale, et al., "Identification of arctigenin as an antitumor agent having the ability to eliminate the tolerance of cancer cells to nutrient starvation," *Cancer Research.*, vol. 66, No. 3, pp. 1751-1757 (Feb. 2006).

Hirose et al., "Effects of arctiin on PhIP-induced mammary, colon and pancreatic carcinogenesis in female Sprague-Dawley rats and MeIQx-induced hepatocarcinogenesis in male F344 rats," *Cancer Letters*, vol. 155 No. 1 pp. 79-88, Jul. 3, 2000.

Takasaki, et al., "Anti-tumor-promoting activity of lignans from the aerial part of *Saussurea medusa," Cancer Letters*, vol. 158, No. 1, pp. 53-59, Sep. 9, 2000.

European Patent Office, Germany, *European Search Report and Written Opinion* . . . International Application No. PCT/JP2011/072049, dated Aug. 11, 2014 (7 pages).

Moritani et al., "Cytotoxic Components of Bardanae Fructus (Goboshi)," *Biol. Pharm. Bull.*, vol. 19, No. 11, pp. 1515-1517 (Nov. 1996).

Miyoshi et al., "Cytotoxic Effects of Arctigenin on Pancreatic Tumor Growth," Cancer Phys. Project, Nat'l Cancer Ctr. Hosp. East, 1 page Abstract (p. 464).

Miyoshi et al., "Arctigenin inhibits pancreatic tumor growth in combination with common chemotherapeutics," Cancer Phys. Project, Nat'l Cancer Ctr. Hosp. East, 1 page Abstract (p. 347).

Ou et al., "Preparastion of the arctigenin by the arctiin hydrolysis using the β-glucosidase," *Pharm. Biotech.*, vol. 16, No. 5, pp. 443-446 (2009).

(Continued)

*Primary Examiner* — Michael Meller
(74) *Attorney, Agent, or Firm* — Sunstein Kann Murphy & Timbers LLP

(57) ABSTRACT

PROBLEM TO BE SOLVED

The present invention is intended to provide a burdock fruit extract comprising arctigenin and arctiin at a definite ratio and a method for producing the same. More particularly, the present invention is intended to provide a method for producing a burdock fruit extract comprising arctigenin and arctiin at a weight ratio of approximately 1:1.

SOLUTION

A method for producing a burdock fruit extract comprising arctigenin and arctiin at a weight ratio of arctigenin/arctiin=0.7 to 1.3 is provided, including the steps of: cutting a burdock fruit and converting arctiin which is inherent in the burdock fruit into arctigenin by enzymatic conversion by beta-glucosidase which is inherent in the burdock fruit, wherein the enzymatic conversion includes reaction at a temperature from 20° C. to 50° C. Also provided is the method further including a step of extracting an extract comprising arctigenin and arctiin by adding an organic solvent and heating to reflux.

3 Claims, No Drawings

(56) References Cited

OTHER PUBLICATIONS

Ou et al., Machine translation (English): "Preparation of the arctigenin by the arctiin hydrolysis using the β-glucosidase," *Pharm. Biotech.*, vol. 16, No. 5, pp. 443-446 (2009).
International Searching Authority, In Japanese: *International Search Report and Written Opinion of the International Searching Authority* . . . International Application No. PCT/JP2011/072049, dated Dec. 20, 2011 (5 pages).
International Searching Authority, English Translation of the *International Search Report and Written Opinion of the International Searching Authority* . . . International Application No. PCT/JP2011/072049, dated Dec. 20, 2011 (5 pages).

* cited by examiner

BURDOCK FRUIT EXTRACT CONTAINING ARCTIGENIN AND METHOD FOR PRODUCING SAME

CROSS-REFERENCE TO RELATED APPLICATIONS

This application is a continuation-in-part of Patent Cooperation Treaty Patent Application PCT/JP2011/072049 filed Sep. 27, 2011; which in turn claims priority from JP 2010-215118, filed Sep. 27, 2010; both of which are incorporated herein by reference in their entirety.

FIELD OF THE INVENTION

The present invention relates to a method for producing a burdock fruit extract containing arctigenin and arctiin. More particularly, the present invention relates to a method for producing a burdock fruit extract containing arctigenin and arctiin at a weight ratio of arctigenin/arctiin=0.7 to 1.3.

BACKGROUND ART

In the Japanese Pharmacopoeia 15th edition, a burdock fruit is defined as a fruit of burdock, Arctium lappa Linne (Compositae). In addition, a burdock fruit is a herbal medicine prescribed for Gingyo-san, Kufugedoku-to, Shofusan and the like, and is classified into a primary material to be used as a pharmaceutical agent exclusively.

A burdock fruit contains approximately 7% of arctiin which is classified into lignan glycoside and approximately 0.6% of arctigenin which is an aglycone of arctiin.

In recent years, cells derived from pancreas cancer such as PANC-1, AsPC-1, BxPC-1 and KP-3 have strong tolerance to an extreme nutrient starvation state, and the possibility is reported that the elimination of the tolerance may be a new biochemical approach in the cancer therapy (Patent document 1).

It is reported that arctigenin is effective, when screened a material which can release the viability of tumor cells in the undernutrition condition using pancreas cancer cell line PANC-1 (Non-patent document 1). According to the above knowledge, a burdock fruit extract containing arctigenin can be used as an anticancer agent for treating pancreatic cancer.

A burdock fruit which is known currently contains arctigenin at a low content of approximately 0.6%. In addition, it is hard to dissolve in water. Thus, it is extremely difficult to produce a burdock fruit extract containing arctigenin at high content by a conventional hot water extraction method.

In addition, provision of a burdock fruit extract containing a definite content of arctigenin as an active ingredient is desired for use in treatment of pancreatic cancer and the like, however, it is difficult to control the conversion of arctiin into arctigenin so that a definite content of arctigenin which is hard to dissolve in water is contained in the production of the burdock fruit extract containing arctigenin at high content, as described above.

Furthermore, it is found that a burdock fruit extract containing a definite content of arctigenin and arctiin has a particularly excellent anticancer effect when it is used to treat pancreatic cancer and the like. Therefore, a method for production that can control the content of arctigenin and arctiin to a definite content is desired in the production of a burdock fruit extract containing arctigenin at high content. Particularly, a method to make it possible to produce a burdock fruit extract containing arctigenin and arctiin at a weight ratio of approximately 1:1 is desired.

PRIOR ART DOCUMENTS

Patent Document

Patent document 1: Japanese Kokai Publication No. 2002-065298

Non-Patent Document

Non-patent document 1: S. AwaLe, J. Lu, S. K. KaLauni, Y. Kurashima, Y. Tezuka, S. Kadota, H. Esumi, Cancer Res., 2006, 66 (3), 1751-1757).

SUMMARY OF THE INVENTION

Problem to be Solved by the Invention

The present invention is intended to provide a burdock fruit extract containing arctigenin and arctiin at a definite ratio and a method for producing the same. More particularly, the present invention is intended to provide a method for producing a burdock fruit extract containing arctigenin and arctiin at a weight ratio of approximately 1:1.

Means to Solve the Problem

As a result of the diligent investigation in order to solve the above problem, the inventors found a technique to adjust the content ratio of arctigenin to arctiin by adjusting the enzyme activity of a burdock fruit as a raw material, the particle size of the cut burdock fruit, the temperature when enzymatically converting arctiin into arctigenin and the temperature when extracting arctigenin and arctiin from the burdock fruit.

The present invention provides a method for producing a burdock fruit extract containing arctigenin and arctiin at a weight ratio of arctigenin/arctiin=0.7 to 1.3 (mole ratio of 1.0 to 1.9), including the steps of: cutting a burdock fruit, and converting arctiin which is inherent in the burdock fruit into arctigenin by enzymatic conversion by beta-glucosidase which is inherent in the burdock fruit, wherein the enzymatic conversion includes a reaction at a temperature from 20° C. to 50° C.

In addition, the present invention provides the method for producing the burdock fruit extract, wherein the burdock fruit is cut to a particle size from 0.85 mm to 9.5 mm in the step of cutting.

Furthermore, the present invention provides the method for producing the burdock fruit extract, wherein the enzyme activity of the beta-glucosidase which is inherent in the burdock fruit is 0.4 U or more per 1 g of the burdock fruit.

In addition, the present invention provides the method for producing the burdock fruit extract, including a step of extracting an extract containing arctigenin and arctiin by adding an organic solvent after the step of enzymatic conversion.

In addition, the present invention provides the method for producing the burdock fruit extract, wherein the organic solvent is ethanol.

In addition, the present invention provides the method for producing the burdock fruit extract, wherein the extract is extracted at approximately 80° C. in the extraction step.

Furthermore, the present invention provides a burdock fruit extract containing arctigenin and arctiin at a weight ratio of arctigenin/arctiin=0.7 to 1.3 which is provided by the method.

Furthermore, the present invention provides an anticancer agent containing a burdock fruit extract containing arctigenin and arctiin at a weight ratio of arctigenin/arctiin=0.7 to 1.3 which is provided by the method.

Effect of the Invention

According to the invention, a burdock fruit extract containing arctigenin which has an antitumor effect at a definite content ratio of arctigenin/arctiin (weight ratio)=0.7 to 1.3 can be provided. Particularly, stable growth inhibition of the tumor and the antitumor effect can be expected by administering the extract to a patient suffering from pancreatic cancer. In addition, the productivity at the time of the production can be improved.

EMBODIMENT FOR CARRYING OUT THE INVENTION

The present invention is described below in detail. The disclosed conditions are examples, and the present invention is not limited to them.

A burdock fruit extract of the present invention is prepared through a step of cutting a herbal medicine, an extraction step (an enzymatic conversion step and an extraction step by an organic solvent), a step of separating solid and liquid, a concentrating step and a drying step.

(Step of Cutting Herbal Medicine)

In the method for producing the burdock fruit extract of the present invention, the burdock fruit which is a raw material is cut into a size suitable for the extraction. The herbal medicine which is a raw material is various parts of plant, mineral or animal and the like, which have various kinds of size, shape and hardness, and have to be cut according to the characteristic. The burdock fruit can be cut using any means well known to those skilled in the art. For example, a commercial cutting machine can be used.

In the method for producing the burdock fruit extract of the present invention, the activity of beta-glucosidase which is an enzyme inherent in the burdock fruit can be measured beforehand for the selection of the burdock fruit suitable for the present invention.

For a method for measuring the activity of beta-glucosidase, for example, a ground product of a burdock fruit is acted on p-nitrophenyl-beta-D-glucopyranoside ($C_{12}H_{15}NO_8$: molecular weight 301.25) (manufactured by SIGMA-ALDRICH) as a substrate to generate p-nitrophenol, and the enzyme activity can be measured by measuring the variation of the absorbance at 400 nm. For the unit representing the enzyme activity, the enzyme level generating 1 μmol of p-nitrophenol per minute can be expressed as 1 unit (U).

In order to provide the burdock fruit extract containing arctigenin and arctiin at a weight ratio of arctigenin/arctiin=0.7 to 1.3, a burdock fruit can be used wherein the activity of the beta-glucosidase which is inherent in the burdock fruit is 0.4 U/g or more, preferably 1 U/g or more.

When it is lower than 0.4 U/g, the hydrolysis is insufficient, the weight ratio of arctigenin decreases and the desired burdock fruit extract cannot be obtained efficiently.

In addition, in the method for producing the burdock fruit extract of the present invention, a burdock fruit which is cut into an arbitrary particle size can be used. The smaller the particle size of the cut burdock fruit is, the more the enzymatic conversion may be promoted and the yield of the extract may be increased. On the other hand, if the particle size is too small, the control of the process may become difficult because the enzymatic conversion is too fast, and a trouble may occur for the accurate solid-liquid separation in the subsequent step.

In order to provide the burdock fruit extract containing arctigenin and arctiin at a weight ratio of arctigenin/arctiin=0.7 to 1.3, as shown in the following EXAMPLES, the burdock fruit is cut into a particle size of 9.5 mm or less, for example, the burdock fruit is cut so that all of the burdock fruit particles pass through a sieve of 9.5 mm.

In addition, in order to provide the burdock fruit extract containing arctigenin and arctiin at a weight ratio of arctigenin/arctiin=0.7 to 1.3, it is desirable that the burdock fruit is cut so that all of the burdock fruit particles pass through a sieve of 9.5 mm and, for example, 60 to 100% are distributed on a sieve of 0.85 mm, and more preferably, 65 to 80% are distributed on a sieve of 0.85 mm.

(Extraction Step)

The extraction step is the most important step in terms of quality among steps of producing a powder of the herbal medicine extract. Due to this extraction step, the quality of the powder of the herbal medicine extract is decided. In the method for producing the burdock fruit extract of the present invention, two stages of the enzymatic conversion step and the extraction step using an organic solvent are carried out to extract the burdock fruit extract.

(Enzymatic Conversion Step)

The enzymatic conversion step is an important step in the method for producing the burdock fruit extract of the present invention. The enzymatic conversion step is a step of enzymatically converting arctiin contained in the burdock fruit into arctigenin by beta-glucosidase which is an enzyme inherent in the burdock fruit.

Specifically, the cut burdock fruit prepared by the above steps is retained at an appropriate temperature to make the beta-glucosidase function and progress the reaction from arctiin to arctigenin.

For example, an arbitrary solution such as water is added to the cut burdock fruit and stirred at a temperature such as around 30° C., and thereby the burdock fruit can be retained at an arbitrary temperature.

In order to provide the burdock fruit extract containing arctigenin and arctiin at a weight ratio of arctigenin/arctiin=0.7 to 1.3, the cut burdock fruit is retained at a temperature of around 30° C., such as a temperature between 20 to 50° C.

When it is lower than 20° C., the hydrolysis is insufficient, the weight ratio of arctigenin decreases and the desired burdock fruit extract cannot be obtained efficiently. On the other hand, when it is higher than 50° C., the enzyme is deactivated, and the weight ratio of arctigenin is decreased and the desired burdock fruit extract cannot be obtained efficiently.

In addition, the length of time for retaining is not limited particularly, as far as the burdock fruit is retained at the above temperature, and for example, it can be retained for approximately 30 minutes. By retaining at 20 to 50° C., an appropriate amount of arctiin is enzymatically converted into arctigenin regardless of the length of time for retaining, and the burdock fruit extract containing arctigenin and arctiin at a weight ratio of approximately 1:1 can be obtained.

(Extraction Step Using Organic Solvent)

The extraction step using an organic solvent is a step of extracting arctigenin and arctiin from the burdock fruit using any appropriate organic solvent. In other words, it is a step of extracting the burdock fruit extract by adding an appropriate solvent in the state in which the content of arctigenin is increased after the above step of enzymatic conversion. For example, an appropriate solvent is added to the burdock fruit extract, and the mixture is heated and stirred for an appropriate length of time to extract the burdock fruit extract. In addition, the burdock fruit extract can be extracted using any extraction method well known to those skilled in the art such as a method of heating to reflux, a method of drip extraction, a method of dipping extraction or a method of pressurized extraction, other than the heating and stirring method.

Because arctigenin is hardly soluble in water, the yield of arctigenin can be improved by adding an organic solvent. Any organic solvent can be used as the organic solvent. For example, alcohols such as methanol, ethanol and propanol as well as acetone can be used. In consideration of safety, ethanol is preferably used as the organic solvent in the method for producing the burdock fruit extract of the present invention.

If the burdock fruit extract is extracted by the heating and stirring, the heating and stirring can be carried out at any temperature, however, the burdock fruit is retained at a temperature of 80° C. or more, such as a temperature between 80 to 90° C. in order to provide the burdock fruit extract containing arctigenin and arctiin at a weight ratio of arctigenin/arctiin=0.7 to 1.3.

In addition, the length of time for the heating and stirring is not limited particularly, as far as the burdock fruit is heated and stirred at the above temperature, and arctigenin and arctiin can be extracted from the burdock fruit into the solvent by the heating and stirring the burdock fruit for approximately 30 minutes, such as 30 to 60 minutes.

The longer the length of time for the heating and stirring is, the more the yield of arctigenin and arctiin is improved. However, if the length of time for the heating and stirring is longer, larger amounts of unnecessary oils and fats begin to dissolve, and the load of the concentrating step becomes larger. Therefore, the length of time for the heating and stirring should be determined appropriately according to the situation.

In addition, the larger the amount of ethanol is, the higher the solubility of arctigenin and arctiin and the more the yield of arctigenin and arctiin is improved. However, if the amount of ethanol is large, larger amounts of unnecessary oils and fats begin to dissolve, and the load of the concentrating step becomes larger. Therefore, the added amount should be determined appropriately according to the situation. Note that the burdock fruit extract can be sterilized and pasteurized simultaneously by the heating and stirring in this step.

(Step of Separating Solid and Liquid)

The step of separating solid and liquid is a step of separating the burdock fruit subjected to the extraction from the extract liquid. The solid-liquid separation can be carried out using any method well known to those skilled in the art. The method for solid-liquid separation includes, for example, a filtration method, a sedimentation method and a centrifugal separation method. Industrially, a centrifugal separation method is desirable.

(Concentrating Step)

The concentrating step is a step of removing the solvent from the burdock fruit extract liquid prior to drying. The removal of the solvent from the burdock fruit extract liquid can be carried out using any method well known to those skilled in the art.

However, it is preferable for the extract liquid from the burdock fruit provided by the above steps not to be exposed furthermore to a high temperature for a long time.

For example, the burdock fruit extract liquid can be concentrated without being exposed to a high temperature for a long time by using a decompression concentration method.

The burdock fruit extract liquid can be concentrated until the burdock fruit extract with a desired concentration can be obtained.

For example, it is desirable to concentrate the extract liquid to the extent that the drying can be carried out appropriately in the following drying step. Alternatively, when the burdock fruit extract is dried and formulated into a powder in the following steps, it is desirable to concentrate the extract liquid until appropriate properties of the formulation can be obtained.

Because arctigenin and arctiin are hardly soluble in water, a large quantity of arctigenin and arctiin adhere in the manufacturing apparatus in the following drying step, and thereby the final yield is largely decreased. Thus, dextrin can be added to the burdock fruit extract liquid provided in this concentrating step in order to prevent the adhesion of arctigenin and arctiin to the manufacturing apparatus. For example, the amount of the added dextrin is preferably around 15 to 30% relative to the solid content of the concentrated liquid.

(Drying Step)

It is a step of finishing the burdock fruit extract provided by the above steps into a powder form. The drying can be carried out using any method well known to those skilled in the art. For example, freeze-drying and spray drying are known as a drying method, and it is common to use the former for laboratory scale production and the latter for mass production.

The burdock fruit extract containing arctigenin and arctiin at a weight ratio of arctigenin/arctiin=0.7 to 1.3 can be provided by the above production process. The method for producing the burdock fruit extract of the present invention must include a step of enzymatic conversion at a temperature from 20° C. to 50° C., however it is not necessary to include all of the other steps.

(Anticancer Agent Containing Burdock Fruit Extract)

Arctigenin which is the major component of the burdock fruit extract is known to act as an active ingredient of an anticancer agent for treating pancreatic cancer. In addition, it has been found that the anticancer agent containing the burdock fruit extract as an active ingredient has the most: superior anticancer effect when arctigenin and arctiin are contained in the burdock fruit extract at a weight ratio of approximately 1:1.

On the other hand, the powder of the extract provided by the method for producing the burdock fruit extract of the present invention contains arctigenin and arctiin at a weight ratio of arctigenin/arctiin=0.7 to 1.3, as described above. Therefore, the powder of the extract provided by the method for producing the burdock fruit extract of the present invention can be used as an anticancer agent having a superior anticancer effect in comparison with the conventional burdock fruit extract.

The anticancer agent containing the extract provided by the method for producing the burdock fruit extract of the present invention can be a composition containing any further components. For example, the anticancer agent containing the extract of the present invention can be provided as pharmaceutical composition together with a pharmaceutically acceptable base, carrier, excipient, disintegrator, lubricant, coloring agent and the like.

Examples of the carrier and the excipient used for the pharmaceutical composition include lactose, glucose, saccharose, mannitol, dextrin, potato starch, corn starch, calcium carbonate, calcium phosphate, calcium sulfate, and crystalline cellulose.

Examples of the binder include starch, gelatin, syrup, gum tragacanth, polyvinyl alcohol, polyvinyl ether, polyvinyl pyrrolidone, hydroxypropyl cellulose, methyl cellulose, ethyl cellulose and carboxymethyl cellulose.

In addition, examples of the disintegrator include starch, agar, gelatin powder, crystalline cellulose, calcium carbonate, sodium hydrogen carbonate, sodium alginate, sodium carboxymethylcellulose and carboxymethylcellulose calcium.

In addition, examples of the lubricant include magnesium stearate, hydrogenated vegetable oil, talc and macrogol. Moreover, any coloring agent permitted to be added to a pharmaceutical agent can be used as the coloring agent.

In addition, if necessary, the pharmaceutical composition may be coated with one or more layers using saccharose, gelatin, purified shellac, gelatin, glycerin, sorbitol, ethyl cellulose, hydroxypropyl cellulose, hydroxypropyl methylcellulose, polyvinylpyrrolidone, cellulose acetate phthalate, hydroxypropyl methylcellulose phthalate, methyl methacrylate and methacrylic acid polymer.

In addition, if necessary, a pH regulator, a buffer, a stabilizer, a solubilizer and the like may be added.

In addition, the pharmaceutical composition can be provided as a formulation in any form. For example, as an orally administered formulation, the pharmaceutical composition can be a tablet such as a sugar-coated tablet, a buccal tablet, a coated tablet or a chewable tablet, a capsule such as a troche, a pill, a powder or a soft capsule, a granule, a suspension, an emulsion, a syrup such as a dry syrup or a liquid formulation such as an elixir.

Alternatively, the pharmaceutical composition can be a formulation for administration such as intravenous injection, subcutaneous injection, intraperitoneal injection, intramuscular injection, percutaneous administration, nasal administration, pulmonary administration, enteral administration, intraoral administration and transmucosal administration for parenteral administration. For example, it can be an injectable solution, a percutaneous absorption tape, an aerosol or a suppository. In addition, the powder of the extract can be a masked formulation or a film coated agent coated with a coating agent, because the powder of the extract has a special acrid taste.

On the other hand, the powder of the extract provided by the method for producing the burdock fruit extract of the present invention can be used as it is. Alternatively, it can be added to a food or the like. In addition, the powder of the extract provided by the method for producing the burdock fruit extract of the present invention can be provided as a food material by being added to, mixed with or applied to other foods. Other than foods, it can be provided as cosmetics, feed and the like.

TEST EXAMPLES

The influence on arctigenin/arctiin (weight ratio) caused by the enzyme activity of the burdock fruit and the condition of the enzymatic conversion (temperature and length of time), namely, the cause and effect relationship of both, was verified.

(Measurement of Enzyme Activity)

Burdock fruits differing in production regions and lots were pulverized by a Wiley mill, and 0.1 g of each pulverized burdock fruit was diluted with 10 mL of water as a sample solution.

As a substrate solution, water was added to 0.15 g of p-nitrophenyl-beta-D-glucopyranoside and the volume was fixed at 25 mL to prepare a 20 mmol/L aqueous solution of p-nitrophenyl-beta-D-glucopyranoside. 0.5 mL of the 20 mmol/L aqueous solution of p-nitrophenyl-beta-D-glucopyranoside was added to 1 mL of a 0.1 mol/L acetate buffer to prepare a cocktail and the cocktail was preheated at 37° C. for approximately 5 minutes.

0.5 mL of the sample solution was added to the cocktail and they were reacted at 37° C. for 15 minutes, and then 2 mL of a 0.2 mol/L aqueous solution of sodium carbonate as a reaction stop solution was added to stop the reaction. The absorbance of this solution at 400 nm was measured and the enzyme activity was calculated based on the variation from the blank solution that was not subjected to the enzymatic reaction using the following formula.

Enzyme activity (U/g)=(Absorbance of the sample solution−Absorbance of the blank solution)×4 mL×1/18.1 (Millimolar molecular extinction coefficient of p-nitrophenol under the above measurement condition: $cm^2/\mu mol$)×1/Light path length (cm)×1/Reaction time (minute)×1/0.5 mL×1/Sample solution level (g/mL)

It was confirmed that the enzyme activity of each burdock fruit was 0.12 to 8.23 U/g as shown in Table 1.

Test Example 1

7 mL of water was added to 1 g of the cut burdock fruit having an enzyme activity of 0.12, 0.27 or 0.40 U/g (Samples 1 to 3), and the temperature conditions for the enzymatic reaction were set to 15° C. and 20° C. and the reaction time at respective reaction temperature was set to 30 minutes. Ethanol was added after the reaction, and the extraction was carried out at 80° C., arctigenin and arctiin of the obtained extract were quantitated, and the weight ratio of arctigenin/arctiin was calculated.

The results are shown in Comparative Examples 1 to 2 and Example 1 of Table 1.

In Sample 3 having an enzyme activity of 0.40 U/g, a burdock fruit extract with arctigenin/arctiin (weight ratio)=0.82 was obtained when the temperature of the enzymatic reaction was 20° C. and the reaction time was 30 minutes.

On the other hand, arctigenin/arctiin (weight ratio) was 0.69 when the temperature of the enzymatic reaction was 15° C. and the reaction time was 30 minutes, thus the temperature of the enzymatic reaction is preferably 20° C. or more.

In addition, Samples 1 and 2 having an enzyme activity of less than 0.40 U/g could not satisfy arctigenin/arctiin (weight ratio)=0.70 or more even if the temperature of the enzymatic reaction was 20° C., thus the enzyme activity of the burdock fruit is preferably 0.40 U/g or more.

Test Example 2

7 mL of water was added to 1 g of the cut burdock fruit having an enzyme activity of 4.03 U/g (Sample 5), the temperature conditions for the enzymatic reaction were set to 30° C., 40° C., 50° C. and 60° C. and the reaction time at respective reaction temperature was set to 15 minutes and 30 minutes (only 30° C. and 60° C.). The extraction was carried out using ethanol after the reaction, and arctigenin and arctiin of the obtained extract were quantitated, and the weight ratio of arctigenin/arctiin was calculated.

The results are shown in Example 3 of Table 1. The burdock fruit extracts with arctigenin/arctiin (weight ratio)=0.7 when the temperature of the enzymatic reaction was 30° C. and the reaction time was 15 minutes, with arctigenin/arctiin (weight ratio)=1.0 when the temperature of the enzymatic reaction was 30° C. and the reaction time was 30 minutes, with arctigenin/arctiin (weight ratio)=1.2 when the temperature of the enzymatic reaction was 40° C. and the reaction time was 15 minutes, and with arctigenin/arctiin (weight ratio)=1.2 when the temperature of the enzymatic reaction was 50° C. and the reaction time was 15 minutes, were obtained.

On the other hand, arctigenin/arctiin (weight ratio) was 0.4 when the temperature of the enzymatic reaction was 60° C. and the reaction time was 15 minutes and arctigenin/arctiin (weight ratio) was 0.5 when the temperature of the enzymatic reaction was 60° C. and the reaction time was 30 minutes.

Based upon the foregoing, the temperature of the enzymatic reaction is preferably less than 60° C.

Test Example 3

7 mL of water was added to 1 g of the cut burdock fruit having an enzyme activity of 1.42 U/g (Sample 4), the temperature condition for the enzymatic reaction was set to 25° C. and the reaction time was set to 10 minutes and 30 minutes. The extraction was carried out using ethanol after the reaction, and arctigenin and arctiin of the obtained extract were quantitated, and the weight ratio of arctigenin/arctiin was calculated.

The results are shown in Example 2 of Table 1. The burdock fruit extracts with arctigenin/arctiin (weight ratio)=0.74 when the temperature of the enzymatic reaction was 25° C. and the reaction time was 10 minutes and with arctigenin/arctiin (weight ratio)=0.85 when the temperature of the enzymatic reaction was the same and the reaction time was 30 minutes, were obtained.

Based upon the foregoing, even if the enzyme activity was 1.42 U/g, desired results were able to be obtained.

Example 7

Production of Burdock Fruit Extract 2

A burdock fruit (enzyme activity was 8.23 U/g) was cut, and all the particles passed through a sieve of 9.5 mm were further passed through a sieve of 0.85 mm and confirmed that 75% of them were remained. After 80 kg of this chopped burdock fruit was added to 560 L of water kept warm at 30 to 33° C. and stirred for 30 minutes, 265 L of ethanol was added and the temperature was raised to 85° C., and the mixture was further heated to reflux for 30 minutes. This solution was centrifuged and a burdock fruit extract liquid was obtained. This operation was repeated two times and the obtained extract liquids were combined, and vacuum concentration was carried out, and 20% of dextrin relative to the solid content of the extract was added and the mixture was spray dried. The arctigenin content and the arctiin content were 6.0% and 6.8% respectively, and a powder of the burdock fruit extract with arctigenin/arctiin (weight ratio)=0.87 (containing 20% of dextrin) was obtained.

TABLE 1

| sample | | | Comparative example 1 Sample 1 | Comparative example 2 Sample 2 | Example 1 Sample 3 | Example 2 Sample 4 | Example 3 Sample 5 | Example 4 Sample 6 | Example 5 Sample 7 |
|---|---|---|---|---|---|---|---|---|---|
| enzyme activity (U/g) | | | 0.12 | 0.27 | 0.40 | 1.42 | 4.03 | 7.82 | 8.23 |
| arctigenin/ | 15° C. | 30 min | 0.26 | 0.50 | 0.69 | — | — | — | — |
| arctiin | 20° C. | 30 min | 0.23 | 0.60 | 0.82 | — | — | — | — |
| (weight | 25° C. | 10 min | — | — | — | 0.74 | — | — | — |
| ratio) | | 30 min | — | — | — | 0.85 | — | — | — |
| | 30° C. | 15 min | — | — | — | — | 0.70 | — | — |
| | | 30 min | — | — | — | — | 1.00 | 0.93 | 0.89 |
| | 40° C. | 15 min | — | — | — | — | 1.20 | — | — |
| | | 30 min | — | — | — | — | — | — | — |
| | 50° C. | 15 min | — | — | — | — | 1.20 | — | — |
| | | 30 min | — | — | — | — | — | — | — |
| | 60° C. | 15 min | — | — | — | — | 0.40 | — | — |
| | | 30 min | — | — | — | — | 0.50 | — | — |

EXAMPLES

Example 6

Production of Burdock Fruit Extract 1

A burdock fruit (enzyme activity was 8.23 U/g) was cut, and all the particles passed through a sieve of 9.5 mm were further passed through a sieve of 0.85 mm and confirmed that 75% of them were remained. 80 kg of this chopped burdock fruit was added to 560 L of water kept warm at 29 to 33° C. and stirred for 30 minutes. Then, 265 L of ethanol was added and the temperature was raised to 85° C., and the mixture was further heated to reflux for 60 minutes. This solution was centrifuged and a burdock fruit extract liquid was obtained. This operation was repeated two times and the obtained extract liquids were combined, and vacuum concentration was carried out, and 20% of dextrin relative to the solid content of the extract was added and the mixture was spray dried. The arctigenin content and the arctiin content were 6.2% and 7.1% respectively, and a powder of the burdock fruit extract with arctigenin/arctiin (weight ratio)=0.89 (containing 20% of dextrin) was obtained.

Example 8

Production of Burdock Fruit Extract 3

A burdock fruit (enzyme activity was 7.82 U/g) was cut, and all the particles passed through a sieve of 9.5 mm were further passed through a sieve of 0.85 mm and confirmed that 75% of them were remained. 80 kg of this chopped burdock fruit was added to 560 L of water kept warm at 30 to 32° C. and stirred for 40 minutes, and after 60 minutes, 258 L of ethanol was added and the temperature was raised to 85° C., and the mixture was further heated to reflux for 30 minutes. This solution was centrifuged and a burdock fruit extract liquid was obtained. This operation was repeated two times and the obtained extract liquids were combined, and vacuum concentration was carried out, 20% of dextrin relative to the solid content of the extract was added and the mixture was spray dried. The arctigenin content and the arctiin content were 6.2% and 6.7% respectively, and a powder of the burdock fruit extract with arctigenin/arctiin (weight ratio)=0.93 (containing 20% of dextrin) was obtained.

Example 9

Production of Burdock Fruit Extract 4

A burdock fruit (enzyme activity was 7.82 U/g) was cut, and all the particles passed through a sieve of 9.5 mm were further passed through a sieve of 0.85 mm and confirmed that 75% of them were remained. After 80 kg of this chopped burdock fruit was added to 560 L of water kept warm at 30 to 32° C. and stirred for 30 minutes, 253 L of ethanol was added and the temperature was raised to 85° C., and the mixture was further heated to reflux for 40 minutes. This solution was centrifuged and a burdock fruit extract liquid was obtained. This operation was repeated two times and the obtained extract liquids were combined, and vacuum concentration was carried out, 25% of dextrin relative to the solid content of the extract was added and the mixture was spray dried. The arctigenin content and the arctiin content were 6.4% and 7.2% respectively, and a powder of the burdock fruit extract with arctigenin/arctiin (weight ratio)=0.89 (containing 25% of dextrin) was obtained.

TABLE 2

| | | Example 6 | Example 7 | Example 8 | Example 9 |
|---|---|---|---|---|---|
| burdock fruit | enzyme activity | 8.23 | 8.23 | 7.82 | 7.82 |
| step of cutting | particle size (mm) | 0.85-9.5 | 0.85-9.5 | 0.85-9.5 | 0.85-9.5 |
| step of enzymatic conversion | temperature (° C.) | 29 to 33° C. | 30 to 33° C. | 30 to 32° C. | 30 to 32° C. |
| | time (min) | 30 min | 30 min | 40 min | 30 min |
| extraction step | solvent | ethanol | ethanol | ethanol | ethanol |
| | temperature (° C.) | 85° C. | 85° C. | 85° C. | 85° C. |
| | time (min) | 60 min | 30 min | 30 min | 40 min |
| step of separating solid and liquid | | centrifugal separation | centrifugal separation | centrifugal separation | centrifugal separation |
| concentrating step | | vacuum concentration | vacuum concentration | vacuum concentration | vacuum concentration |
| drying step | | spray drying | spray drying | spray drying | spray drying |
| arctigenin/arctiin (weight ratio) | | 0.89 | 0.87 | 0.93 | 0.89 |

From the results of the above Examples 6 to 9, it was found that a burdock fruit extract with the content of arctigenin: arctiin (weight ratio)=approximately 1:1 can be provided by enzymatically converting arctiin into arctigenin at approximately 30° C. in the step of enzymatic conversion. A reaction caused by an enzyme usually progresses dependent on the temperature and the length of time, however, it was found that, at the above temperature, a burdock fruit extract with the content of arctigenin:arctiin (weight ratio)=approximately 1:1 can be obtained regardless of the length of time for the enzymatic conversion.

In addition, from the results of the above Examples 6 to 9, it was found that a burdock fruit extract with the content of arctigenin:arctiin (weight ratio)=approximately 1:1 can be obtained by raising the temperature to approximately 85° C. for heating to reflux in the step of heating to reflux. Usually, when the heating to reflux is carried out to obtain an extract, the amount of the ingredient within the extract changes dependent on the temperature and the length of time, however, it was found that, at the above temperature, a burdock fruit extract with the content of arctigenin:arctiin (weight ratio)=approximately 1:1 can be obtained regardless of length of time for heating to reflux.

| Example 10 Granule formulated with powder of burdock fruit extract | |
|---|---|
| (1) Burdock fruit extract powder of Example 7 | 33.3% |
| (2) Lactose | 65.2% |
| (3) Hydroxypropyl cellulose | 1.5% |
| Total | 100% |

Method for Production

A granule was produced according to the paragraph of Granule in the General Rules for Preparations of "Japanese Pharmacopoeia". That is, the ingredients from (1) to (3) described in the above list were taken and produced into a granule form. Each 1.5 g of the granular material was packed into an aluminum laminate film, and a granule containing 0.5 g of the burdock fruit extract powder per one package was obtained.

| Example 11 Tablet formulated with powder of burdock fruit extract | |
|---|---|
| (1) Burdock fruit extract powder of Example 7 | 37.0% |
| (2) Crystalline cellulose | 45.1% |
| (3) Carmellose calcium | 10.0% |
| (4) Crospovidone | 3.5% |
| (5) Hydrous silicon dioxide | 3.4% |
| (6) Magnesium stearate | 1.0% |
| Total | 100% |

Method for Production

A tablet was produced according to the paragraph of Tablet in the General Rules for Preparations of "Japanese Pharmacopoeia". That is, the ingredients from (1) to (6) described in the above list were taken and produced into the tablet.

Various embodiments of the present invention may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for producing a burdock fruit extract containing arctigenin and arctiin at a weight ratio of arctigenin/arctiin=0.7 to 1.3 from a burdock fruit which inherently comprises arctiin and beta-glucosidase, the method comprising the steps of:

cutting a burdock fruit, adding water to said cut burdock fruit, and stirring said cut burdock fruit to a temperature of 20° C. to 50° C. to permit enzymatic conversion of arctiin into arctigenin by beta-glucosidase, to produce a burdock fruit extract, wherein the enzyme activity of said beta-glucosidase is 0.4 U or greater per 1 g of said burdock fruit, and further comprising an extraction step which comprises adding an organic solvent to said burdock fruit extract, wherein the burdock fruit is retained at a temperature of 80° C. or higher during said extraction step to yield the burdock fruit extract containing arctigenin and arctiin at a weight ratio of arctigenin/arctiin=0.7 to 1.3 from a burdock fruit which inherently comprises arctiin and beta-glucosidase.

2. The method according to claim 1, wherein said burdock fruit is cut to a particle size of from 0.85 mm to 9.5 mm in said cutting step.

3. The method according to claim 1, wherein said organic solvent is ethanol.

* * * * *